(12) United States Patent
Nace

(10) Patent No.: US 10,085,869 B2
(45) Date of Patent: *Oct. 2, 2018

(54) KNEE ORTHOSIS FOR TREATMENT OF PCL INJURY

(71) Applicant: Medical Alliance, S.A., San Jose (CR)

(72) Inventor: Richard A Nace, San Jose (CR)

(*) Notice: Subject to any disclaimer, the term of this patent is extended or adjusted under 35 U.S.C. 154(b) by 115 days.

This patent is subject to a terminal disclaimer.

(21) Appl. No.: 14/748,610

(22) Filed: Jun. 24, 2015

(65) Prior Publication Data

US 2015/0290010 A1   Oct. 15, 2015

Related U.S. Application Data

(63) Continuation-in-part of application No. 13/648,515, filed on Oct. 10, 2012, now Pat. No. 9,089,403, which is a continuation-in-part of application No. 12/469,671, filed on May 20, 2009, now Pat. No. 8,308,669, application No. 14/748,610, filed on Jun. 24, 2015, which is a continuation-in-part of application No. 13/864,310, filed on Apr. 17, 2013, now Pat. No. 9,265,646.

(60) Provisional application No. 61/054,516, filed on May 20, 2008.

(51) Int. Cl.
*A61F 5/01* (2006.01)
*A61F 5/34* (2006.01)

(52) U.S. Cl.
CPC .......... *A61F 5/012* (2013.01); *A61F 5/0123* (2013.01); *A61F 5/0125* (2013.01); *A61F 5/34* (2013.01); *A61F 2005/0137* (2013.01); *A61F 2005/0165* (2013.01); *A61F 2005/0172* (2013.01); *A61F 2005/0179* (2013.01)

(58) Field of Classification Search
CPC .................. A61F 5/0123; A61F 5/0125; A61F 2005/0169; A61F 2005/0179
See application file for complete search history.

(56) References Cited

U.S. PATENT DOCUMENTS

| | | | |
|---|---|---|---|
| 4,353,361 A | 10/1982 | Foster | |
| 4,370,977 A * | 2/1983 | Mauldin | A61F 5/0125 602/16 |
| 4,503,846 A | 3/1985 | Martin | |
| 4,606,542 A | 8/1986 | Segal | |
| 4,865,024 A * | 9/1989 | Hensley | A61F 5/0123 602/16 |
| 4,991,571 A * | 2/1991 | Kausek | A61F 5/0123 602/16 |
| 5,121,742 A | 6/1992 | Engen | |
| 5,415,625 A * | 5/1995 | Cassford | A61F 5/012 602/13 |
| 5,514,081 A | 5/1996 | Mann | |
| 5,520,622 A * | 5/1996 | Bastyr | A61F 5/012 602/13 |
| 5,785,673 A * | 7/1998 | Billotti | A61F 5/0109 128/DIG. 20 |
| 5,865,166 A | 2/1999 | Fitzpatrick | |

(Continued)

*Primary Examiner* — Keri J Nelson

(74) *Attorney, Agent, or Firm* — Larson & Larson, P.A.; Justin P. Miller; Frank Liebenow

(57) ABSTRACT

A disclosed knee orthosis has provides support to the knee of a patient with a damaged or severed posterior cruciate ligament by supporting the knee with a brace, and providing an air bladder to create force against the rear of the tibia.

13 Claims, 11 Drawing Sheets

(56) References Cited

U.S. PATENT DOCUMENTS

| | | | |
|---|---|---|---|
| RE37,209 E * | 6/2001 | Hensley | A61F 5/0123 602/26 |
| 6,527,733 B1 | 3/2003 | Ceriani et al. | |
| 7,048,704 B2 * | 5/2006 | Sieller | A61F 5/0125 602/16 |
| 7,306,572 B2 * | 12/2007 | Ceriani | A61F 5/0123 602/16 |
| 7,410,472 B2 * | 8/2008 | Yakimovich | A61F 5/0125 602/16 |
| 7,918,812 B2 | 4/2011 | Knecht | |
| 8,308,669 B2 | 11/2012 | Nace | |
| 8,376,974 B2 | 2/2013 | Nace | |
| 8,672,865 B2 | 3/2014 | Franke | |
| 2002/0133108 A1 | 9/2002 | Jagodzinski | |
| 2005/0240135 A1 * | 10/2005 | Hoffmeier | A61F 5/0123 602/26 |
| 2008/0188784 A1 * | 8/2008 | Ceriani | A61F 5/0123 602/16 |
| 2008/0294079 A1 * | 11/2008 | Sterling | A61F 5/012 602/13 |
| 2010/0323859 A1 | 12/2010 | Von Hoffmann | |
| 2010/0331750 A1 * | 12/2010 | Ingimundarson | A61F 5/0123 602/26 |
| 2011/0105969 A1 | 5/2011 | Nace | |
| 2011/0152736 A1 | 6/2011 | Ng | |
| 2014/0276250 A1 | 9/2014 | Branch | |

* cited by examiner

KNEE ORTHOSIS FOR TREATMENT OF PCL INJURY

CROSS-REFERENCE TO RELATED APPLICATION

This application is a continuation-in-part of U.S. patent application Ser. No. 13/648,515 filed Oct. 10, 2012, which in turn is a continuation-in-part of U.S. patent application Ser. No. 12/469,671, filed May 20, 2009, which in turn claims priority to U.S. Provisional Application for Patent No. 61/054,516 filed May 20, 2008.

This application is further a continuation-in-part of U.S. patent application Ser. No. 13/864,310, filed Apr. 17, 2013. The disclosure of all applications is hereby incorporated by reference.

FIELD

The invention relates to a knee orthosis. More particularly, it refers to a pre-operative, post-operative knee orthosis for stabilizing a knee joint of a person before or after surgery or after injury thereto, that applies an adjustable corrective and therapeutic force to the knee joint and surrounding muscles above and below the knee and that optionally removes pressure from a lower shin cuff of the knee orthosis when a patient using the novel knee orthosis of this present invention flexes the knee joint or performs a body squatting motion through rotation about a shin cuff hinge.

BACKGROUND

Orthosis devices and appliances commonly referred to as "orthotics," are known in the prior art and have been utilized for many years by orthotists (a maker and fitter of orthotics), physical therapists, and occupational therapists to assist in the rehabilitation of a patient's joints and associated limbs or adjacent skeletal parts of the patient's body related to a variety of conditions. An early example can be seen in U.S. Pat. No. 3,581,741 to Rosman, which discloses a knee brace comprising an upper rigid body portion and a lower rigid body portion pivotably coupled together on the lateral side in a manner so that they may pivot relative to each other about an axis generally perpendicular to the zone of overlap and may slide relative to each other in all radial directions generally parallel to the zone of overlap.

Webster's New College Dictionary defines "orthotics" as a branch of mechanical medical science that deals with the support and bracing of weak or ineffective joints or muscles. The word "ortho" actually comes from Greek and means "to straighten." Orthotics are used to support, straighten, and stabilize affected joints and assist to correct normal human function as closely as possible. Orthotics used as knee braces have typically been designed to support and protect the knee joint that is associated with a variety of knee joint conditions, for alleviating pain associated with joint movement at the particular location being treated or for immobilizing the knee joint so that movement thereof in either the medial or lateral directions or rotation of the knee is eliminated or at least significantly reduced.

Repetitive use of a joint, such as the knee, over time tends to reduce the stability of the knee. In cases of injury through accident or sports related causes, instability of the knee can be exacerbated and worsened to the point that without immobilization or support of the knee joint by an orthotic, a person cannot bear the weight of their own body upon the knee joint. Or to do so results in great pain, which is usually treated with pain medications that can be addictive and hard on the liver and other important organs of the body. Further, when there is a lack of movement of a patient due to knee instability, a sedentary lifestyle is usually taken up, which can result in a reduction of body energy, weight gain, atrophied muscles concentrated around the knee joint, and a general depression of mental state due to the lack of ability of the person to be self-sufficient and mobile.

Therefore, it can be plainly seen that knee orthotics of all types are useful if they assist a person in returning to a more normal lifestyle or at least one that is significantly less sedentary when compared to the immobile person with an instable knee. It can be said that proper use of the knee joints is essential to complete body health and a proper state of mind.

It is well known, as complaints are abundant, that not all knee orthotics or braces that stabilize the knee are comfortable to wear. In fact, most knee orthotics apply unwanted pressure to the thigh and the shin of the patient when the patient walks, squats, or flexes the knee joint. This is because all prior art knee orthotics are typically made from very hard and rigid materials that do not flex and move with the changing conditions of the body (i.e., expansion and contraction of the leg musculature). Such areas of change include the knee joint area and the upper and lower leg when the patient is walking, flexing, or squatting. This can be particularly seen with the shin cuff that applies a great amount of pressure against the shin of the patient when the patient squats. This pressure, therefore, discourages the patient from performing any squatting action, which in turns encourages the patient to remain sedentary, resulting in the degradation of physical and mental state.

Further, prior art knee orthotics do not apply therapeutic and corrective forces to the knee joint area and the surrounding leg musculature area. Such is needed in combination with a flexible and pliable brace that incorporates a system for reducing or eliminating pressure placed against the shin of the patient when the patient walks or flexes the knee joint or when he squats his body. This can also include alone or together a system for reducing or eliminating pressure placed against the thigh of the patient when the patient walks or flexes the knee joint or when he squats. The specific elements that accomplish such pressure elimination include, in the present invention, flexible and pliable materials for one or both the shin or thigh cuffs, and hinged shin and thigh cuffs that permit rotation from a 90 degree position to a degree of at least 45 degrees, if not further.

SUMMARY

The knee orthosis of the present invention provides all of the advantages needed, which are mentioned above and that are currently deficient and wholly missing from the prior art. The present knee orthosis is used and indicated for increased medial, lateral, and rotational support and control of the knee joint following injury to, or reconstruction of, the anterior cruciate ligament (ACL) and posterior cruciate ligament (PCL), or protection of the collateral ligament of the knee. The present invention provides increased support for patients who have continued symptoms of significant knee instability such as giving way, which may be due to poor quadriceps or hamstring strength (i.e., hemiplegia), or for patients who have a desire to quickly resume activities after knee surgery. The present knee orthosis is also useful after total knee replacement or high tibia osteotomy.

To provide the above set forth benefits and improvements over the prior art, the present knee orthosis device includes two vertical struts, positioned on opposed sides of a knee joint in a generally parallel relationship, wherein each vertical strut has a hinge member located at a general middle portion thereof, and further wherein each vertical strut has a top and bottom end portion. Both polycentric and uni-centric hinges can be employed for the two hinges members, in any combination thereof. An upper thigh cuff attached at opposed ends to the upper end portions of the two vertical struts provides a means to secure the knee orthosis to the thigh of the patient. A secondary thigh strap is also employed to provide additional securing means and is positioned slightly below the thigh cuff. The thigh cuff is positioned posterior to the thigh, whereas the secondary thigh strap and a strap used to secure the thigh cuff are both positioned anterior to the thigh of the patient.

A shin cuff attaches at opposed ends to the lower end portions of the two vertical struts and is positioned anterior to the shin. The shin cuff has a strap member that wraps around the back of the shin of the patient for securing it to the patient's shin. A secondary shin strap is positioned slightly above the shin cuff but is positioned on the posterior side of the shin area of the patient.

The lower shin cuff has a pair of hinges located proximal to the shin cuff opposed ends and left and right vertical strut lower end portions for permitting the shin cuff to pivot downwardly away from a shin of a person wearing the knee orthosis when a person flexes the knee or performs a squatting motion thereby reducing or eliminating unwanted pressure that is usually applied to the shin of a patient of a person when they flex the knee, walk or squat. The shin cuff can pivot upwards of 60-75 degrees.

The novel knee orthosis of the present invention also employs a plurality of air bladders used as therapeutic 7 and corrective force elements for the device. The air bladders are removably positionable along inner surfaces of the two vertical struts and hinges. Any number from one to six air bladders can be employed such that force can be applied on both sides of the knee joint, at the knee joint, directly above the knee joint on the inner and outer thigh area and directly below the knee joint on the inner and outer shin area. When employed the air bladders also provide additional stabilization to the knee, prevent brace slippage and provide an extra degree of comfort to patient.

The novel knee orthosis also employs elastic thigh and cuff cushion members positioned along the inner surfaces of the thigh and shin cuff, respectively, for providing more comfort and support. The elasticity of these cushions allows them to bend and flex with the movements of the patient but return to their stable positions after movement by the patient such that the patient's knee joint is continuously stabilized regardless of the movement made by the patient using the knee orthosis of the present invention.

In a first alternate embodiment, the upper thigh cuff also has a pair of hinges located proximal to the thigh cuff opposed ends and left and right vertical strut upper end portions for permitting the thigh cuff to pivot upwardly away from a thigh of a person wearing the knee orthosis when a person flexes the knee or performs any other motion thereby reducing or eliminating unwanted pressure that is usually applied to the thigh of a patient of a person when they flex the knee, walk or squat. The thigh cuff can pivot upwards of 60-75 degrees or more.

Additionally disclosed is an embodiment of the brace intended to treat injuries sustained to the posterior cruciate ligament, more commonly referred to as the PCL.

The PCL is but one of the four major knee ligaments. Put simply, the PCL connects the rear of the lower portion of the knee-joint to the front of the upper portion of the knee joint. The lower portion of the knee-joint is part of the tibia, and the upper portion of the knee joint is part of the femur. Connecting the two joints in this way allows the PCL to resist forces that may cause the tibia to move rearward with respect to the femur.

This ability to resist rearward motion makes the PCL critical to proper joint operation. A damaged or torn PCL results in a knee joint that allows the tibia to move rearward, decreasing joint stability and making a patient prone to further injury.

The PCL is commonly injured by loads applied to a flexed knee. For example, forces applied to a leg during a car accident, during which the user's leg is flexed.

The embodiment of the brace disclosed within compensates for damage to the PCL by proving a compensating force through the use of an air bladder placed behind the tibia. A user's knee is strapped into the leg brace, providing lateral stability.

But with the PCL damaged, instability remains because the upper portion of the tibia is permitted to slide rearward, rotating about an axis below the knee. Through the addition of an air bladder below the knee, and behind the tibia, a forward force is created to take the place of the damaged PCL.

The location of the bladder is important. The bladder is placed behind and below the knee, but on the upper portion of the lower leg. Preferable placement focuses the force of the bladder on the upper end of the tibia and fibia, given that this is the location the damaged PCL no longer supports.

The disclosed knee orthosis compensates for a PCL injury by increasing stability of a knee of a patient and decreasing rearward deflection of the patient's tibia. This is accomplished by providing a leg brace with an air bladder affixed to the leg brace such that during use of the leg brace, the air bladder applies pressure to the patient's tibia immediately behind and below the patient's knee, compensating for the injury to the PCL.

The PCL brace may also include the above-disclosed swing assist assembly containing at least one tensile member affixed to a hinge of the leg brace, which acts to straighten the leg brace from a bent position to a straight position. The tensile member used can be an elastic loop, have an O-shaped cross section, and/or may create a continuous force that acts to straighten, or extend, the leg brace. The tensile member, or energy storage mechanism, may act to generate a force proportional to an angle of flexion of the knee brace.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
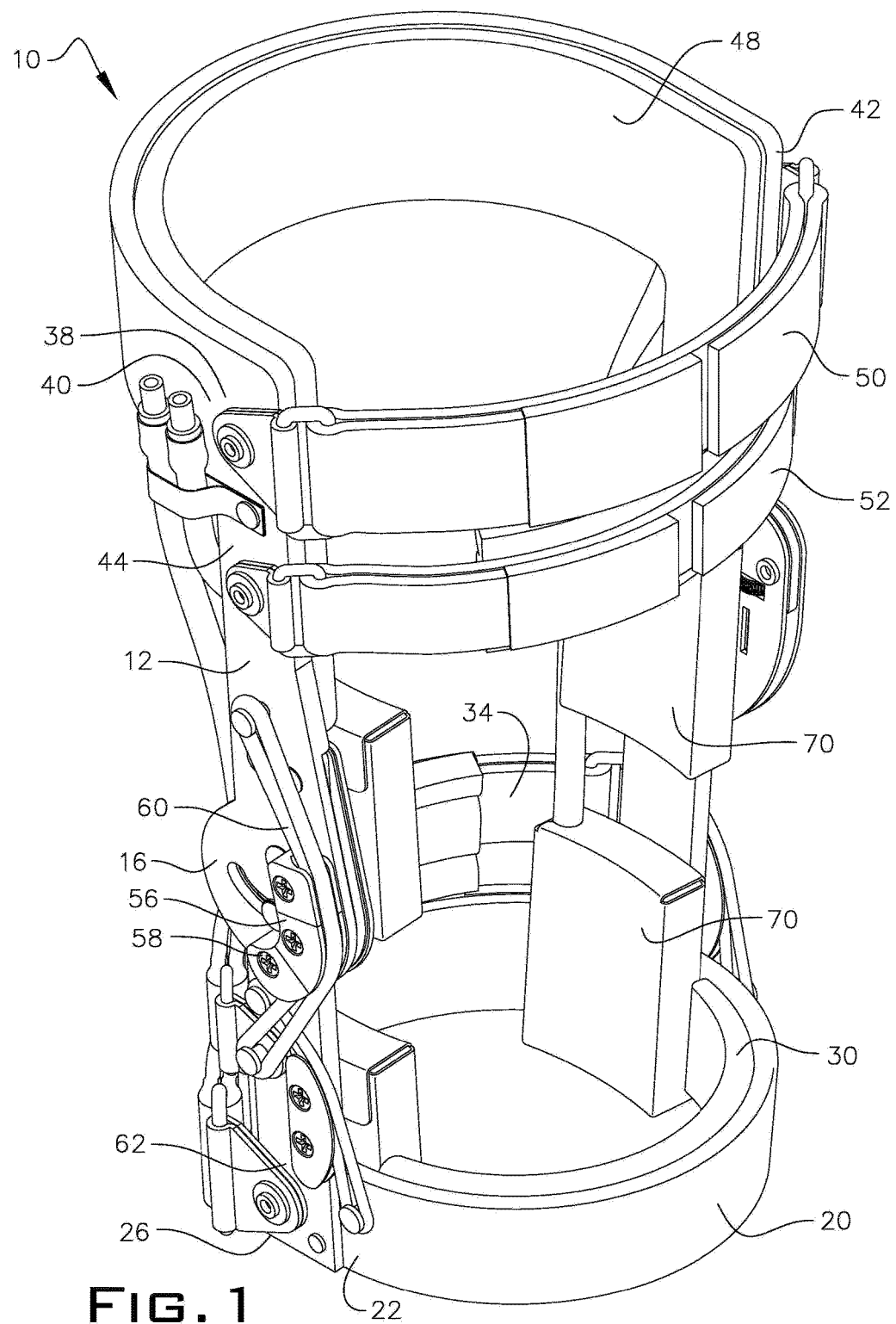
FIG. 1 is a left side perspective view of the knee orthosis of the present invention.

Throughout the following detailed description the same reference numerals refer to the same elements in all figures.

Figure 2:
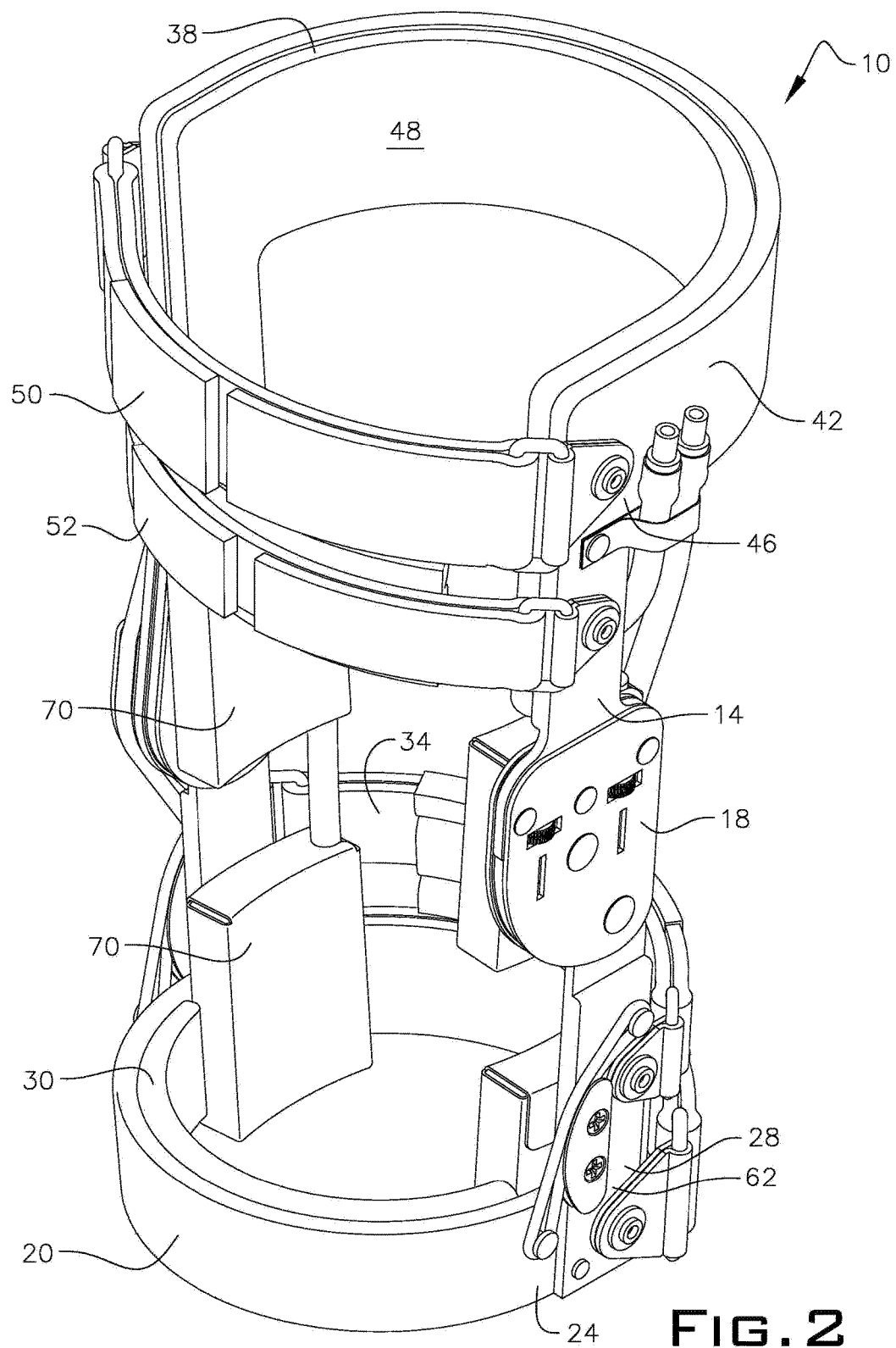
FIG. 2 is a right side perspective view of the knee orthosis of the present invention.

Referring to FIGS. 1 and 2, a knee orthosis 10 of the present is shown. As shown, knee orthosis 10 has a left side and right side vertical strut, 12 and 14, respectively. Struts 12 and 14 are generally parallel and when knee orthosis 10 is employed on a patient, run along medial and lateral sides of a knee joint and thigh and shin area of the patient. Each strut has its own hinge 16 and 18 positioned intermediate top and bottom portions of struts 12 and 14 such that knee orthosis 10 pivots about said hinges when the knee joint of the patient is flexed. In the embodiment shown in FIGS. 1 and 2, hinge 16 is a polycentric hinge and hinge 18 is a uni-centric hinge. However, nothing herein limits the use of knee orthosis to this embodiment shown and described herein in this preferred embodiment could be employed. In fact, any combination of hinges could be employed.

Figure 3:
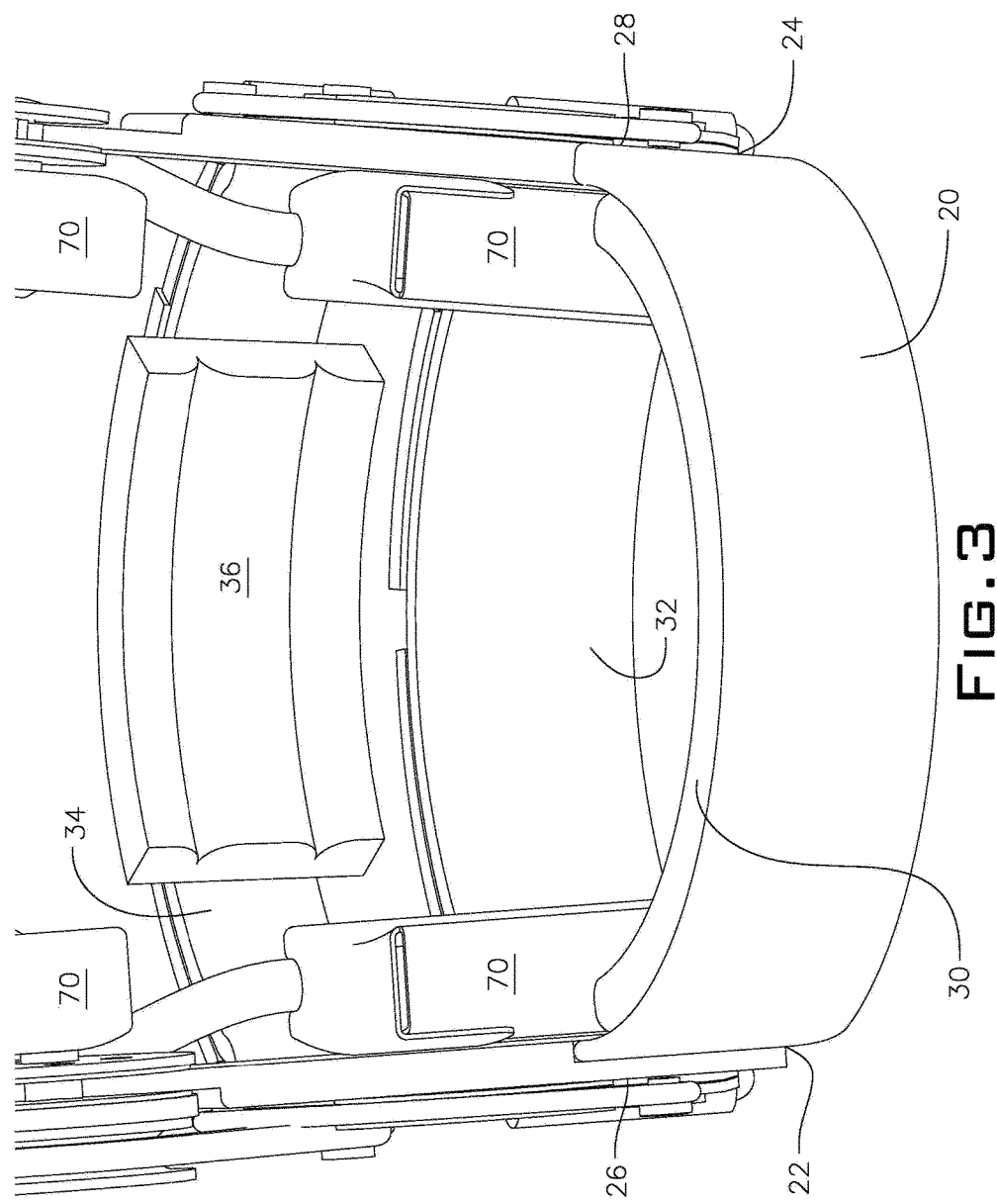
FIG. 3 is a front view of the knee orthosis of the present invention illustrating the shin cuff located at a lower end of the knee orthosis.

Referring to FIG. 3, and also with continuing reference to FIGS. 1 and 2, an anterior positioned shin cuff 20 is shown that has opposed ends 22 and 24. Shin cuff opposed ends 22 and 24 attach to lower ends 26 and 28 of left and right side vertical struts 12 and 14. Attached along an inner surface (not shown) of shin cuff 20 is a flexible shin cushion pad 30 which is removably attached to said shin cuff 20 inner surface. Shin cuff cushion 30 is very pliable, with a shape capable of being manipulated and then able to return to its normal resting state, as shown in FIG. 3. It is attached to shin cuff 20 inner surface by hook and loop material.

With continuing reference to FIG. 3, it is shown that shin cuff 20 has a shin cuff strap 32 that wraps behind the shin of a patient for securing thereto. Further, a secondary shin strap 34, with a positionable cushion pad 36, is positioned slightly above shin cuff strap 32 and is used to provide extra securing means for the knee orthosis 10 to the patient. Both shin cuff strap 32 and secondary shin strap 34 each have opposed ends which loop through D-rings (see FIGS. 5 and 6) and then attach to themselves by hook and loop material.

Figure 4:
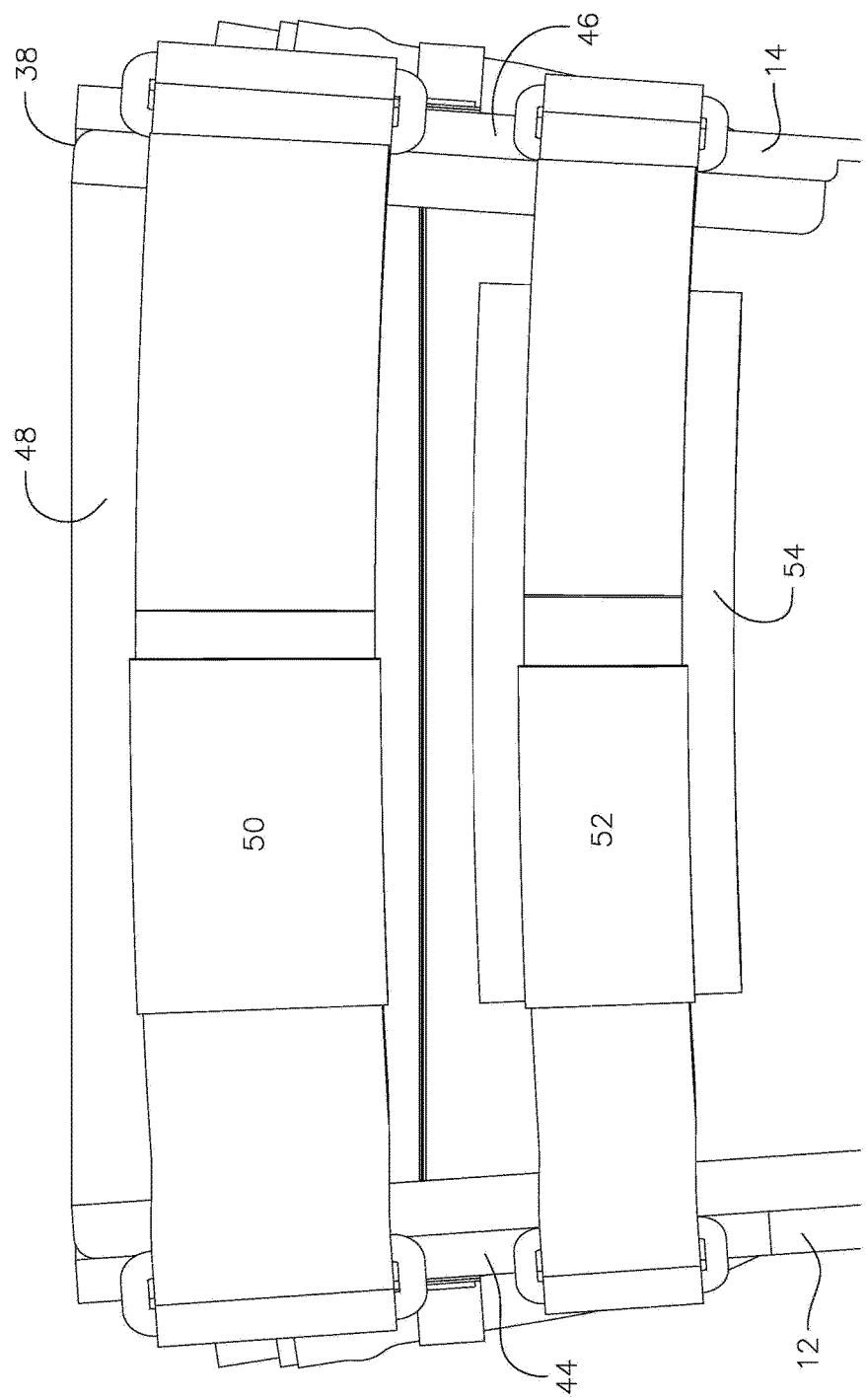
FIG. 4 is a front view of the knee orthosis of the present invention illustrating the thigh cuff located at an upper end of the knee orthosis.

Referring now to FIG. 4, and also with continuing reference to FIGS. 1 and 2, a posterior thigh cuff 38 is shown that has opposed ends 40 and 42. Thigh cuff opposed ends 40 and 42 attach to upper ends 44 and 46 of left and right side vertical struts 12 and 14. Attached along an inner surface (not shown) of thigh cuff 38 is a flexible thigh cushion pad 48 that is removably attached to thigh cuff 38 inner surface.

Thigh cuff cushion pad 48 is very pliable, with a shape capable of being manipulated and then able to return to its normal resting state, as shown in FIG. 4. It is attached to thigh cuff 38 inner surface by hook and loop material.

With continuing reference to FIG. 4, it is shown that thigh cuff 38 has a thigh cuff strap 50 which wraps in front of the thigh of a patient for securing thereto. Further, a secondary thigh strap 52, with a positionable cushion pad 54 is positioned slightly below thigh cuff strap 50 and is used to provide extra securing means for the knee orthosis 10 to the patient. Both thigh cuff strap 50 and secondary thigh strap 52 each have opposed ends which loop through D-rings (see FIGS. 1 and 2) and then attach to themselves by hook and loop material.

Figure 5:
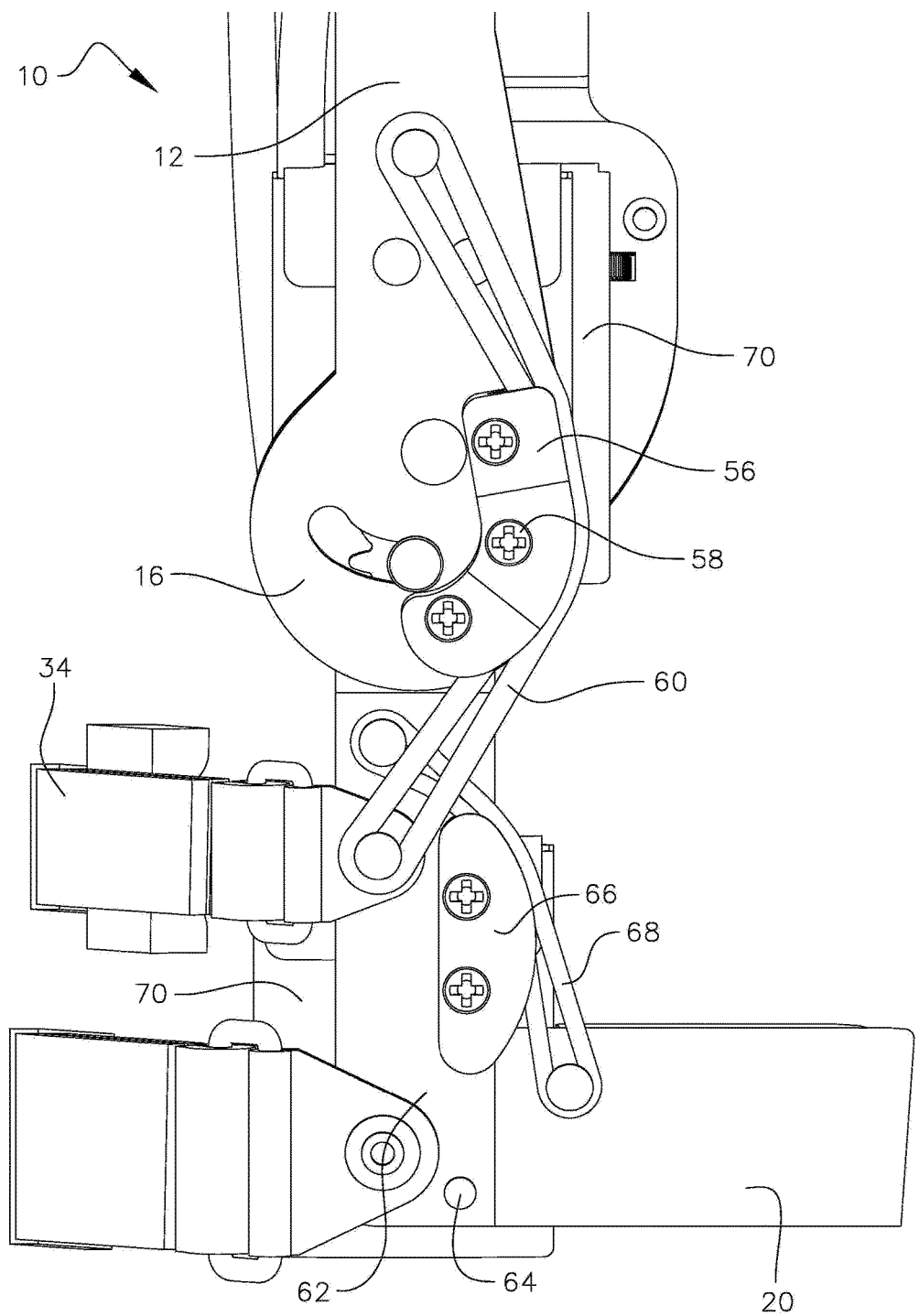
FIG. 5 is a left side view of the knee orthosis of the present invention illustrating a polycentric hinge and deflection guide of a left side vertical strut and a left side shin cuff hinge.

Referring now to FIG. 5, it is shown that polycentric hinge 16 includes a deflection guide 56, which optionally includes a plurality of setting blocks 58 and a tensile member 60. The tensile member 60 is attached at opposed ends to knee orthosis 10, and stretches over the plurality of setting blocks 58 to provide a force to knee orthosis 10 to assist patients in gait kinetics and musculature exercise. The tensile member 60 may be any component capable of providing a tensile force, including but not limited to one or more elastic bands, o-rings, coil springs, rubber bands, or resilient member.

The deflection guide 56 acts to keep the tensile member 60 some distance away from the axis of rotation of the hinge 16/18. If the tensile member is allowed to move beyond the hinge 16/18 it either becomes ineffective by providing no extension force, or counter-productive by creating a bending, rather than extending, force.

Nothing herein limits the use of only one deflection guide 56, nor does anything herein limit which side deflection guide 56 is employed in the case that only one deflection guide 56 is employed with knee orthosis 10, as shown in the preferred embodiment.

When a strut 12/14 is bent across hinge 16/18, the deformation/elongation of tensile member 60 provides a force to aid in leg extension, or straightening of the knee joint. In some examples, the tensile member 60 is in a contracted or relaxed state when the strut 12/14 is in a generally parallel relationship, and in an extended or stretched state when the strut 12/14 is in a generally bent. As a result of creating a force that aids in leg extension, the tensile member 60 acts as a motion accelerating mechanism. The force that is created by the tensile member 60 is either a constant force regardless of length through use of a constant force spring or equivalent, or more commonly the force increases as the tensile member 60 experiences greater deformation/elongation.

Figure 6:
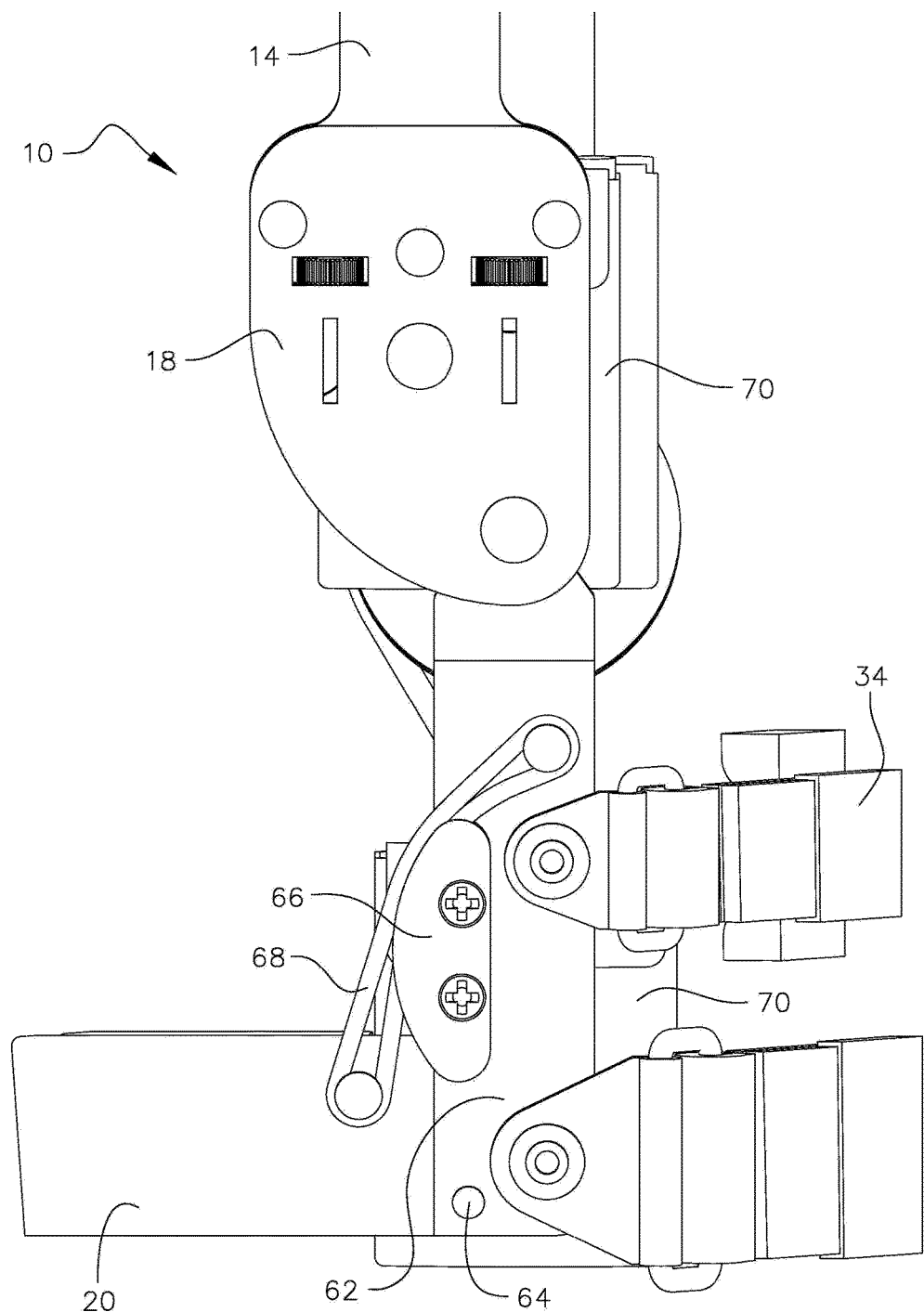
FIG. 6 is a right side view of the knee orthosis of the present invention illustrating a uni-centric hinge and of a right side vertical strut and a right side shin cuff hinge.
Figure 7:
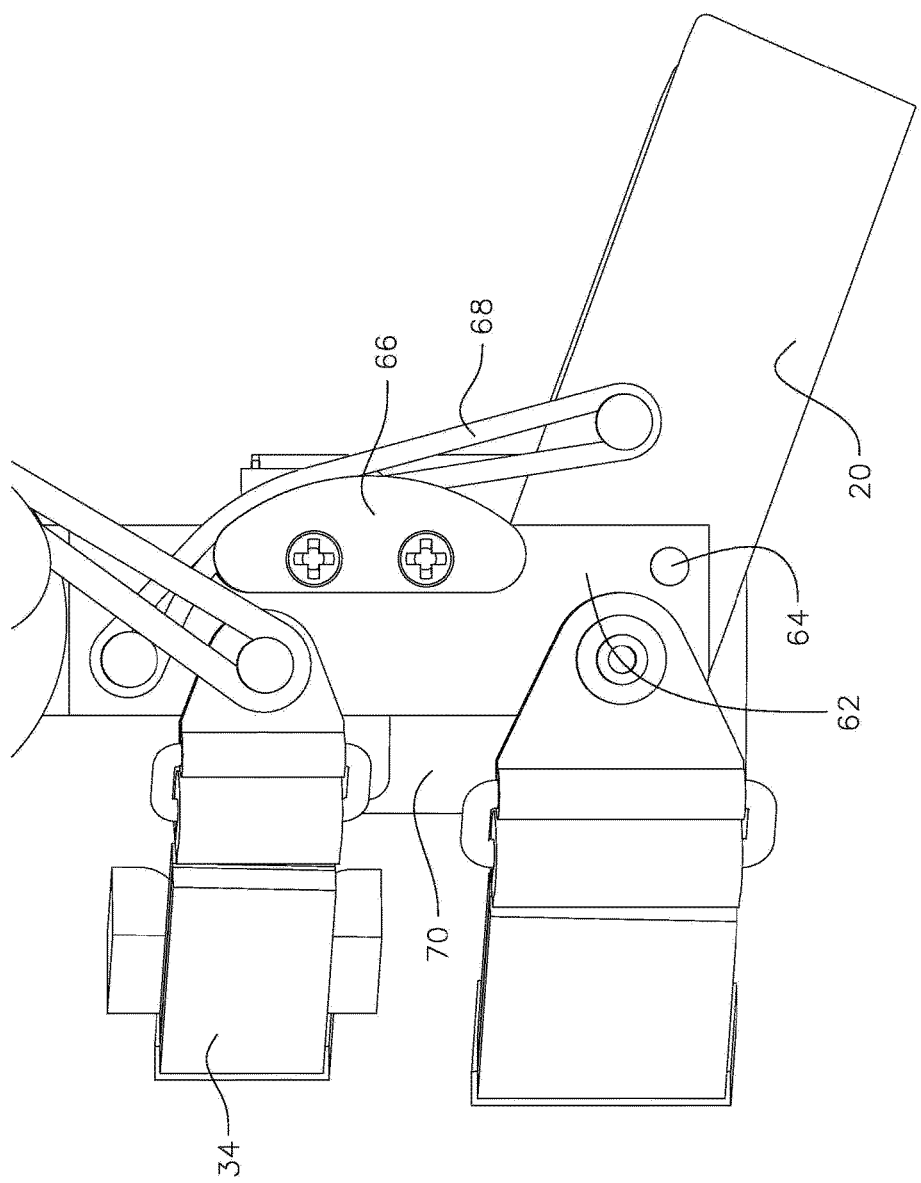
FIG. 7 is a left side view of the knee orthosis of the present invention illustrating how the shin cuff angles downwardly away from a horizontal plane.

Referring now to both FIGS. 5 and 6, it is shown that knee orthosis 10 also includes a shin cuff hinge assembly 62 on both left and right lower ends, 26 and 28, of left and right vertical struts, 12 and 14. Each shin cuff hinge assembly 62 contains a pivoting axis 64, a setting block 66 and a shin tensile member 68, attached at opposed ends to knee orthosis 10, for stretching over setting block 66. The shin tensile member 68 may be any component capable of providing a tensile force, including but not limited to one or more elastic bands, coil springs, rubber bands, or resilient member. As shown in FIG. 7, shin cuff 20 pivots downwardly about both axis 64, so that shin cuff 20 reduces the pressure applied against the shin of the patient when he walks, flexes his knee or squats down. Shin tensile member 68 provides a means to return shin cuff 20 to its normal resting state when the patient ceases to walk, flex his knee or squat down.

Referring back to FIGS. 1 and 2, it can be seen that a plurality of air bladders 70 are employed along inner surfaces of the left and right vertical struts 12 and 14. Bladders 70 are attached to knee orthosis 10 by hook and loop material and are therefore removably attachable. Although only four air bladders 70 are shown, nothing herein limits the use of more or less than four bladders. For example, in an alternate embodiment, six air bladders 70 are employed to provide corrective and therapeutic force to the knee joint area at the knee joint on both sides, above the knee joint on both sides and below the knee joints on both sides.

Figure 8:
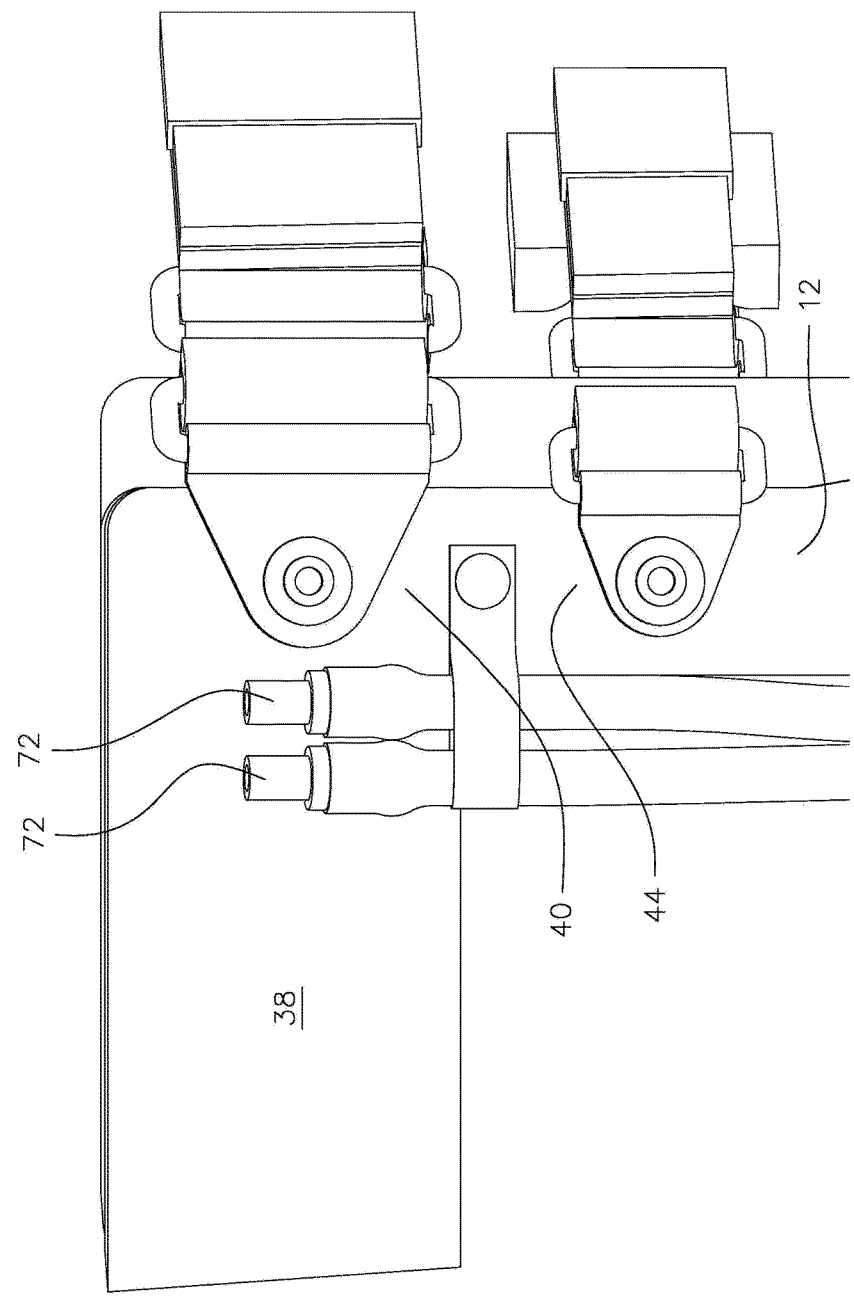
FIG. 8 illustrates the inflation tubes of the air bladders used in conjunction with knee orthosis of the present invention as the therapeutic and corrective force employed to the knee joint area and the surrounding leg musculature.

Referring to FIG. 8, a set of inflation tubes 72 are shown, which are used to inflate or deflate air bladders 70 depending on therapist or patient preferences.

In the preferred embodiment, knee orthosis 10 is made from highly pliable, semi-rigid materials that permit knee orthosis 10 to bend, flex, and move with the movements of the patient, but all the while maintaining the knee in a completely stabilized and immobile state. However, nothing herein limits the use of more rigid, less pliable materials if necessary.

Although not shown, the upper thigh cuff can also employ a pair of hinges located proximal to the thigh cuff opposed ends and left and right vertical strut upper end portions for permitting the thigh cuff to pivot upwardly away from a thigh of a person wearing the knee orthosis when a person flexes the knee or performs any other motion thereby reducing or eliminating unwanted pressure that is usually applied to the thigh of a patient of a person when they flex the knee, walk or squat. The thigh cuff can pivot upwards of 60-75 degrees or more. The present invention can employ a hinged shin cuff, a hinged thigh cuff, or both a hinged shin and hinged thigh cuff.

Figure 9:
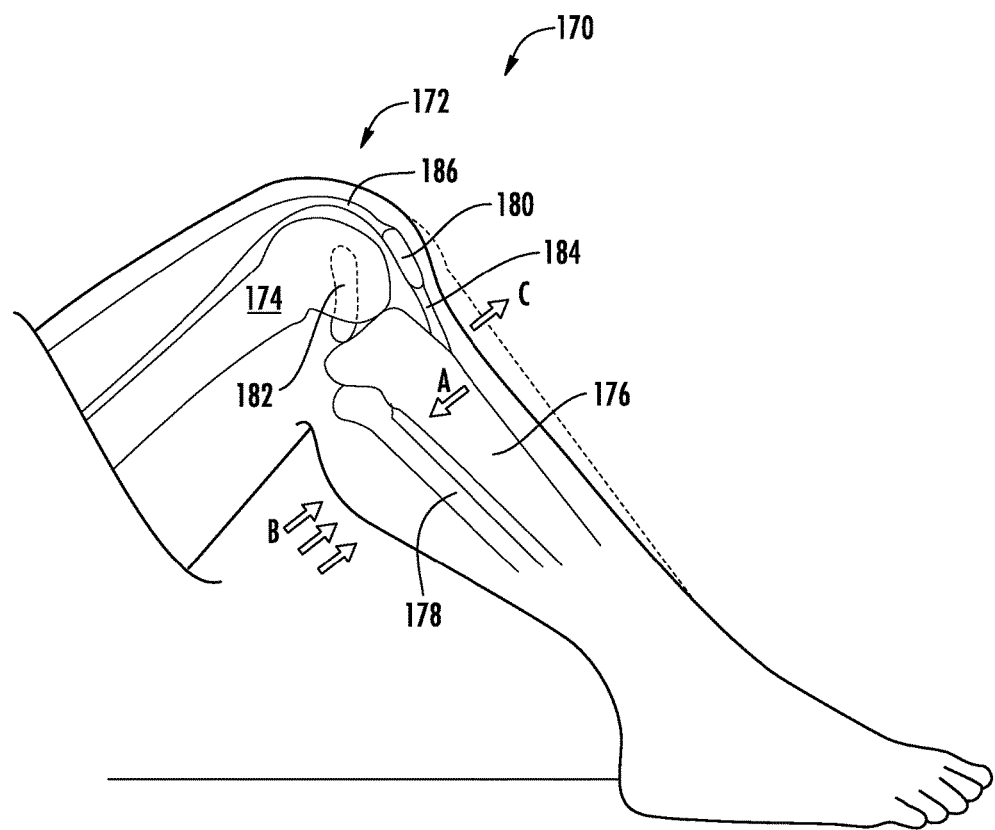
FIG. 9 illustrates an internal view of a lower leg and knee, showing deflection that results from a PCL injury.

Referring to FIG. 9, an internal view of a lower leg and knee with a PCL injury is shown.

The lower leg 170 bends about the knee 172, with the femur 174 being the bone above the knee 172, and the tibia 176 being the bone below the knee 172. The fibia 178 connects to the tibia 176, but does not form part of the knee 172.

The patella (knee cap) 180 is placed generally in front of the knee 172, attached above to the patellar tendon 184 and below to the quadriceps tendon 186.

The PCL 182 is shown connecting the femur 174 to the tibia 176. Given the orientation of the PCL, it is shown that a damaged PCL 182 cannot prevent the rearward movement of the tibia 176, shown by arrow A. What is needed is support from the rear, shown as arrows B. The support guides the tibia 176 forward, shown as arrows C, into the proper position, shown by the dashed line.

Figure 10:
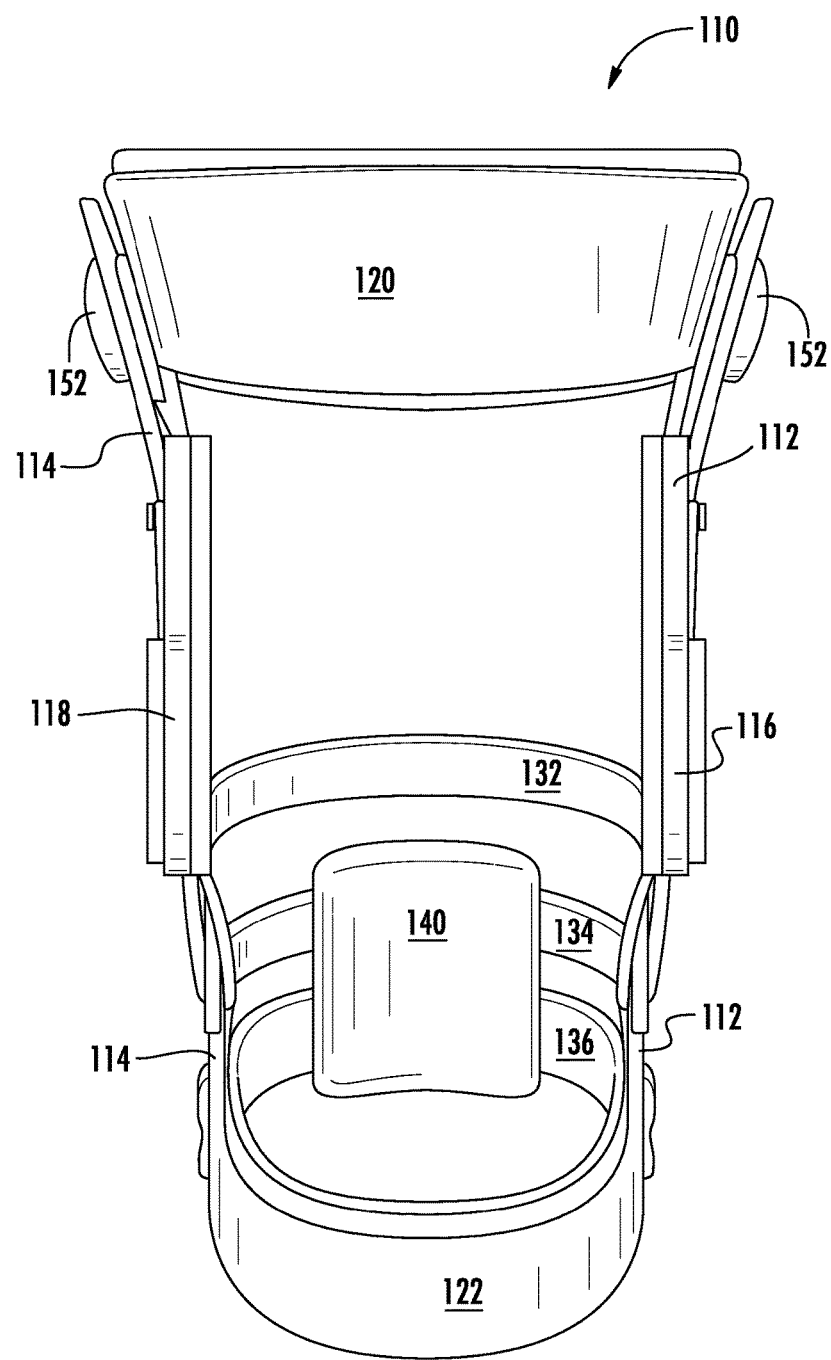
FIG. 10 illustrates a front view of the Knee Orthosis for Treatment of PCL Injury.

Referring to FIG. 10, a front view of the Knee Orthosis for Treatment of PCL Injury is shown.

As shown, PCL orthosis 110 has a left side vertical strut 112 and right side vertical strut 114. The left side vertical strut 112 and right side vertical strut 114 are generally parallel when worn by a patient, affixed along the medial and lateral sides of a knee joint, extending to the thigh and shin area of the patient.

The left side vertical strut 112 includes a left hinge 116 positioned between the top and bottom portions of the strut. Correspondingly, right side vertical strut 114 includes a right hinge 118.

The left hinge 116 and right hinge 118 are positioned to line up with the knee joint of a patient when the leg is flexed. Polycentric hinges are shown, but the hinges can be any combination of polycentric and uni-centric hinges.

Near the top of the PCL orthosis 110, thigh cuff 120 connects the left side vertical strut 112 and right side vertical strut 114 at optional thigh cuff hinges 152. Correspondingly, near the base of the PCL orthosis 110 is shin cuff 122.

PCL bladder 140 can be seen, shown as attached to intermediate shin strap 134 and lower shin strap 136. Also shown is upper shin strap 132.

Figure 11:
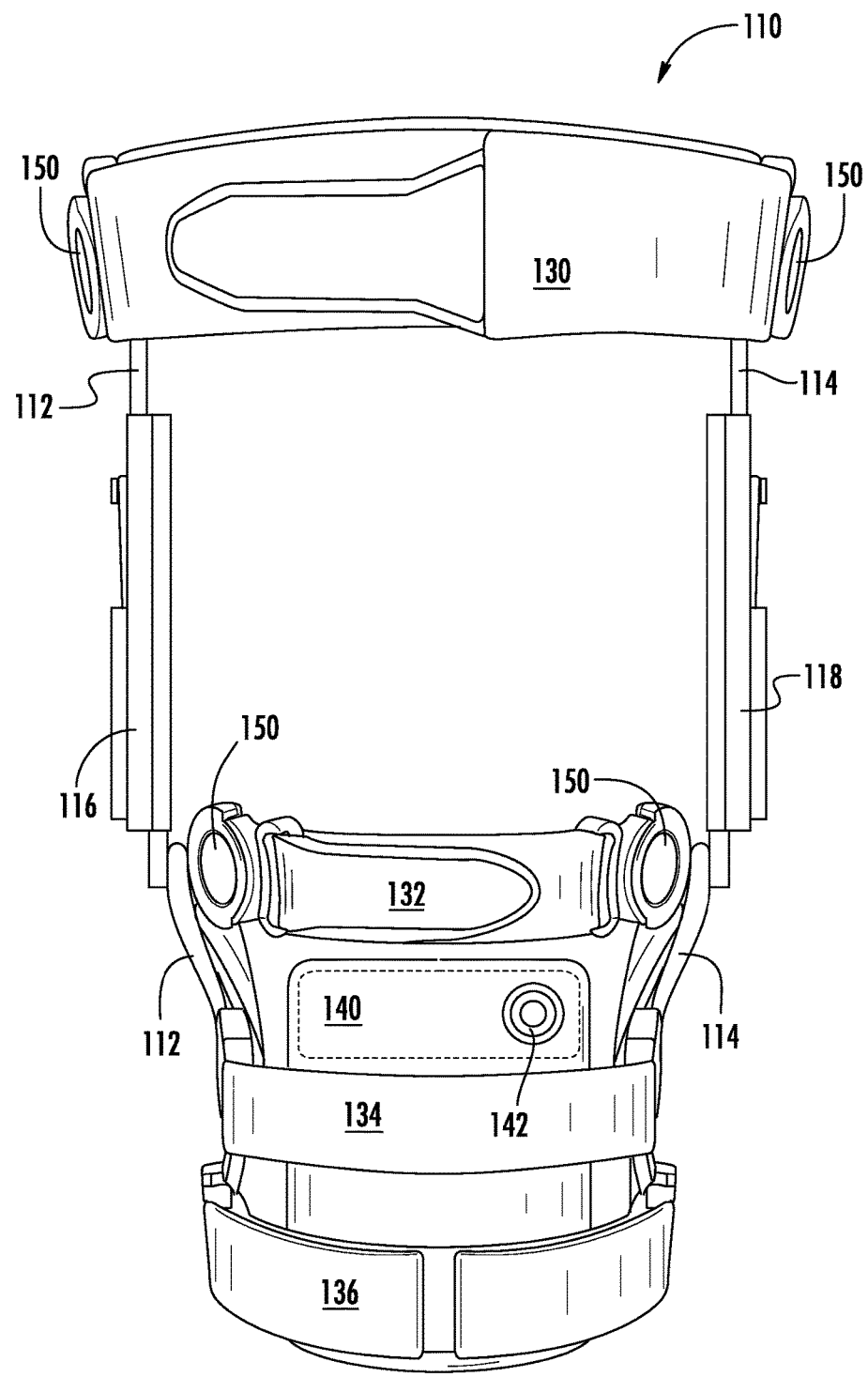
FIG. 11 illustrates a rear view of the Knee Orthosis for Treatment of PCL Injury.

Referring to FIG. 11, a rear view of the Knee Orthosis for Treatment of PCL Injury is shown.

Crossing the patient's leg above the knee is thigh strap 130. Crossing the patient's leg below the knee is upper shin strap 132, intermediate shin strap 134, and lower shin strap 136.

Shown attached to the intermediate shin strap 134 and lower shin strap 136 is the PCL bladder 140. But the PCL bladder can be located differently, as well as attached to a increased or decreased number of straps. The important feature of the PCL bladder 140 is that it creates forward pressure against the rear of the tibia.

A fill nozzle 142 is shown for adding air to the PCL bladder 140. Also shown are optional strap release clips 150.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:

1. A device to compensate for a PCL injury by increasing stability of a knee of a patient and decreasing rearward deflection of a tibia of the patient and unloading the patient's PCL; the device comprising:
   a) a leg brace having a pair of upper struts and a pair of lower struts;
      i) the pair of lower struts having an upper end and a lower end;
      ii) the upper end of the pair of lower struts ending at a pair of hinges;
      iii) the lower end of the pair of lower struts ending at a shin cuff,
         (1) the shin cuff adapted to surround a front of the tibia;
         (2) a lower shin strap adapted to surround a rear of the tibia, the lower shin strap adapted to hold the device in place with respect to the tibia of the patient by applying a first pressure;
   b) an air bladder;
      i) the air bladder affixed to the lower shin strap;
      ii) the air bladder adapted to inflate after the lower shin strap has been secured;
      iii) the air bladder adapted to assert pressure against the tibia at a point above the shin cuff and below the pair of hinges, the pressure of the air bladder adapted to unload the patient's PCL by applying a second pressure, thus preventing further PCL damage.

2. The device of claim 1, further comprising:
   a) a first swing assist assembly containing at least one tensile member affixed to a hinge of the pair of hinges of the leg brace,
      i) the first swing assist assembly acting to straighten the leg brace from a bent position to a straight position.

3. The device of claim 2, wherein the at least one tensile member is an elastic loop adapted to store and release energy created by a user's gait.

4. The device of claim 2, wherein the at least one tensile member is adapted to aid the extension of the knee of the patient by continuously creating a force that acts to straighten, or extend, the leg brace.

5. The device of claim 2, wherein the energy storage mechanism includes at least one tensile member generating a force proportional to an angle of flexion of the knee of the patient.

6. A knee brace for use by a patient to compromise for a damaged PCL by asserting pressure against a tibia of the patient to unload the damaged PCL, the knee brace comprising:
   a) a pair of upper struts and a pair of lower struts;
      i) the pair of lower struts having an upper end and a lower end;
      ii) the upper end of the pair of lower struts ending at a pair of hinges;
      iii) the lower end of the pair of lower struts ending at a shin cuff,
         (1) the shin cuff adapted to surround a front of the tibia;
   b) a lower shin strap adapted to surround a rear of the tibia;
      i) the lower shin strap adapted to hold the knee brace in place with respect to the tibia of the patent by applying a first force;
   c) an energy storage mechanism, the energy storage mechanism continuously gathering energy during leg flexion and releasing energy during leg extension, the energy storage mechanism encouraging a rate of extension of the knee brace, the energy storage mechanism including at least one looped elastic band that stretches and contracts to generate a force proportional to an angle of flexion between an upper strut of the pair of upper struts and a lower strut of the pair of lower struts; and
   d) an air bladder affixed to the lower shin strap;
      i) the air bladder adapted to inflate after the lower shin strap has been secured;
      ii) the air bladder adapted to assert pressure against the tibia at a point above the shin cuff and below the pair of hinges, thereby creating pressure against a patient's tibia, the pressure of the air bladder adapted to unload the patient's PCL by applying a second force, thus preventing further PCL damage.

7. The knee brace of claim 6 further comprising a plurality of adjustable air bladders, the adjustable air bladders configured to apply varying amounts of corrective and therapeutic force to a left side and a right side of the knee of the patient, the varying amounts of force adjustable based on adjustments to air pressure within the adjustable air bladders.

8. The knee brace of claim 6, wherein the at least one looped elastic band has an O-shaped cross section.

9. A knee orthosis comprising:
   a) two vertical struts, adapted to be positioned on opposite sides of a knee joint in a generally parallel relationship,
      i) each of the vertical struts having a hinge member,
      ii) each of the vertical struts having a proximal section and a distal section,
      iii) each proximal section having a proximal end, and
      iv) each distal section having a distal end;
   b) an upper thigh cuff attached at opposed ends to the proximal ends of each of the vertical struts;
   c) a lower shin cuff attached at opposed ends to the distal ends of each of the vertical struts;
   d) a lower shin strap attached at opposed ends to the distal ends of each of the vertical struts;
      i) the lower shin strap adapted to hold the knee orthosis in place by applying a first force to a tibia of a patient;
   e) a PCL compensation bladder attached to the lower shin strap on a side facing the lower shin cuff,
      i) the PCL compensation bladder to be inflated after the lower shin strap is secured;
      ii) the PCL compensation bladder providing pressure at a point above that of the lower shin cuff;
      iii) the pressure of the PCL compensation bladder adapted to unload the patient's PCL by applying a second force, thus preventing further PCL damage;
      iv) the knee orthosis adapted to compensate for a damaged or torn PCL.

10. The knee orthosis of claim 9, further comprising:
    a) a first swing assist assembly containing at least one tensile member affixed to either hinge member of the knee orthosis;
    b) the first swing assist assembly acting to straighten the knee orthosis from a bent position to a straight position.

11. The knee orthosis of claim 10, wherein the first swing assist assembly includes a deflection guide that prevents the at least one tensile member from crossing an axis of either hinge member.

12. The knee orthosis of claim 10, wherein the at least one tensile member is adapted to aid the extension of the knee joint by continuously creating a force that acts to straighten, or extend, the knee orthosis.

13. The knee orthosis of claim 10, wherein the at least one tensile member is a loop.

* * * * *